United States Patent [19]

Zharov

[11] 4,372,149

[45] Feb. 8, 1983

[54] LASER-EXCITED SPECTROPHONE

[76] Inventor: Vladimir P. Zharov, ulitsa Svobody, 48, korpus 1, kv. 8, Moscow, U.S.S.R.

[21] Appl. No.: 207,278

[22] Filed: Nov. 17, 1980

[51] Int. Cl.³ ............................................. G01N 21/00
[52] U.S. Cl. ......................................................... 73/24
[58] Field of Search ................... 73/24; 250/341, 343, 250/351; 356/432, 437

[56] References Cited

U.S. PATENT DOCUMENTS

| | | | |
|---|---|---|---|
| 3,659,452 | 5/1972 | Atwood et al. | 73/23 |
| 4,028,932 | 6/1977 | Rosencwaig | 73/24 |
| 4,163,382 | 8/1979 | Amer | 73/24 |
| 4,303,343 | 12/1981 | Patel et al. | 250/351 |

OTHER PUBLICATIONS

V. P. Zharov et al., "Optoacoustic Laser Spectroscopy of Excited Vibrational Molecular States", *Applied Physics*, vol. 12, No. 1, pp. 15–17, 1977.

T. F. Deutsch, "Optoacoustic Measurements of Energy Absorption in $CO_2$ Tea-Laser Excited $SF_6$ at 293 and 145K", *Optics Letters*, vol. 1, No. 1, pp. 25–17, Jul. 1977.

*Primary Examiner*—Stephen A. Kreitman
*Attorney, Agent, or Firm*—Myron Greenspan

[57] ABSTRACT

A laser-excited spectrophone comprises a working chamber having optical windows at its butt ends to pass through laser radiation, a gaseous sample being contained within a cavity thereof. The cavity of the working chamber communicates with a conduit whose length exceeds 8 to 10 times its cross-sectional diameter, while the volume of said conduit is at least 50 times smaller than the volume of the working chamber. The conduit accommodates a condenser microphone. The laser-excited spectrophone in compliance with the invention controls the temperature of the sample gas contained within the working chamber by its heating with the aid of an individual arrangement.

14 Claims, 1 Drawing Figure

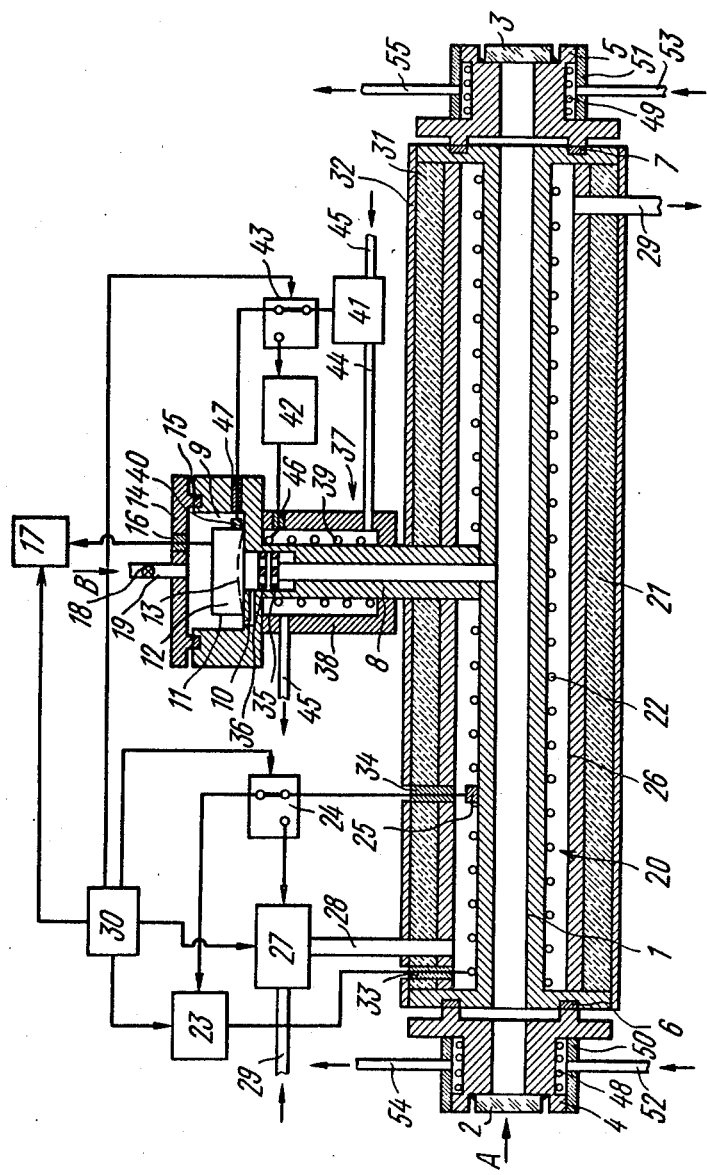

LASER-EXCITED SPECTROPHONE

FIELD OF THE INVENTION

The present invention relates to optical instruments for spectrometric gas analysis, wherein tunable lasers are utilized as sources of radiation. It is particularly directed to laser-excited spectrophones.

The laser-excited spectrophone forming the subject of the present invention may be used in such research applications as measuring weak absorptivities in gaseous media as a function of gas temperature in laser molecular spectroscopy, obtaining absorption spectra of molecular gases over a wide temperature range, and analyzing non-linear and multiple-photon effects and excited vibrational molecular states. It is also suitable for use in applied sciences, say, for increasing selectivity in detecting molecular microimpurities in gases by identifying and discriminating absorption from molecules being detected using known temperature relationships in air pollution problems, checking purity of certain gases, providing a high-sensitivity chromatographic detector, and eliminating adsorption of toxic and aggressive gases on chamber walls, another possible field of application being medical and biological research.

PRIOR ART

Known in the art is a laser-excited spectrophone comprising a working chamber having optical windows on its butt ends to pass through laser radiation and filled with a sample gaseous mixture, and a condenser microphone with a measuring diaphragm fabricated from an organic material and installed in the midportion of the chamber virtually flush with a side wall (cf. U.S. Pat. No. 3,659,452, Int. Cl. G01N 21/26, 1972).

Such a spectrophone may operate only within a comparatively narrow ambient temperature range since it includes no means for controlling temperature within its working chamber.

Another known laser-excited spectrophone operating over a wider temperature range includes a working chamber cooled to 145° K. together with a sample gas (cf. Optics Letters, V. 1, No. 1, 1977, (New York): T. F. Deutsch "Optoacoustic measurement of energy absorption in $CO_2$ TEA laser excited $SF_6$ at 293° and 145° K.," pp. 25–27).

In the aforesaid spectrophone an electret microphone is disposed in the central portion of the working chamber.

However, the temperature range in such a spectrophone is limited, a disadvantage associated with the fact that gas temperature within the working chamber may not be increased above the ambient temperature.

Another known laser-excited spectrophone operating over a wider temperature range comprises a working chamber having optical windows at its butt ends to pass through laser radiation, a means for controlling temperature of a sample gas in the working chamber by its heating incorporating a temperature control element encompassing outer walls of the chamber, a chamber temperature transducer, and a thermoregulator having its input connected to the chamber temperature transducer and an output thereof coupled to the temperature control element, and a condenser microphone mounted in a conduit communicating with the cavity of the working chamber (cf. Applied Physics, V. 12, No. 1, 1977, (Springer-Verlag): V. P. Zharov, V. S. Letokhov and F. A. Ryabov "Optoacoustic laser spectroscopy of excited vibrational molecular states," pp. 15–17).

In the foregoing spectrophone the temperature range is limited being approximately within 290°–560° K., a disadvantage associated with the fact that gas temperature in its working chamber may not be decreased below the ambient temperature.

In such a spectrophone the conduit is relatively short (about 1 cm) and is used solely to locate the microphone conveniently beside the working chamber. With the microphone arranged in the above manner its performance and stability of the basic parameters are degraded with time due to varying physical properties and tension of its measuring diaphragm fabricated from organic material as the temperature thereof changes under the effect of hot gas. In the known spectrophone the gas contained within the working chamber may be heated to about 500°–600° K. for a time as short as 5 to 10 minutes, i.e. for a period over which the sensitivity of the microphone does not substantially change due to relatively slow transfer of heat from the cavity of the working chamber to the microphone.

BRIEF DESCRIPTION OF THE INVENTION

It is an object of the present invention to provide a laser-excited spectrophone operating over a wide temperature range with gas heated to 800° K. and cooled to 100° K.

Another object of the invention is to provide a laser-excited spectrophone operating over a wide temperature range during a long time interval (for at least several hours).

A still another object of the invention is to provide a laser-excited spectrophone operating over a wide temperature range over a long time interval with high threshold sensitivity.

The foregoing and other objects of the invention are accomplished by that in a laser-excited spectrophone comprising a working chamber having optical windows at its butt ends to pass through laser radiation, main means for controlling temperature of a sample gas in the working chamber by its heating including an individual temperature control element encompassing outer walls of the chamber, a chamber temperature transducer and an individual thermoregulator having its input connected to the chamber temperature transducer and an output thereof coupled to the temperature control element, and a condenser microphone mounted in a conduit communicating with the cavity of the working chamber, according to the invention, the conduit has a length exceeding 8 to 10 times its cross-sectional diameter, while volume thereof is at least 50 times smaller than the volume of the working chamber.

Preferably the spectrophone includes an additional means for controlling temperature of the sample gas in the working chamber by its cooling, which comprises an individual temperature control element encompassing the outer walls of the working chamber and an individual thermoregulator having its input connected to the chamber temperature transducer common to the main and additional means and an output thereof coupled to the temperature control element, and a switch connecting the chamber temperature transducer to both individual thermoregulators.

Desirably the conduit includes at least one thermal filter decreasing static temperature fluctuations of the sample gas in the vicinity of the microphone.

Advantageously the thermal filter comprises a perforated metal plate.

It is expedient that the spectrophone incorporates means for controlling temperature of the sample gas in the conduit by, respectively, cooling or heating said sample gas depending on the operation of the main or additional means for controlling temperature of the sample gas in the working chamber heating or cooling said sample gas in the working chamber.

Preferably the means for controlling temperature of the sample gas in the conduit comprises two temperature control elements encompassing the outer walls of the conduit, a microphone temperature transducer and thermoregulators whose number corresponds to the number of the temperature control elements, the inputs of which are connected to the microphone temperature transducer and whose outputs are coupled to the respective temperature control element, and a switch connecting the microphone temperature transducer to the thermoregulators.

The laser-excited spectrophone according to the invention permits analyzing gas absorption over a wide temperature range during a long time interval with high threshold sensitivity.

BRIEF DESCRIPTION OF DRAWING

The foregoing and other objects of the invention will become more apparent in the description of a specific embodiment thereof, taken in conjunction with the accompanying drawing which is a longitudinal sectional view of a laser-excited spectrophone according to the invention.

DETAILED DESCRIPTION OF THE INVENTION

The laser-excited spectrophone forming the subject of the present invention comprises a cylindrical working chamber 1 filled with a gaseous sample, for example, the air and having optical windows 2 and 3 at its butt ends to pass through continuous modulated laser radiation as shown by the arrow A. Use of pulsed laser radiation is also possible.

The windows 2 and 3 are, respectively, secured to shaped flanges 4 and 5 sealed at the butt ends of the working chamber 1 by the use of sealing rings 6 and 7.

The cavity of the working chamber 1 communicates with a cylindrical conduit 8 whose wider portion 9 communicating with the conduit 8 through a capillary tube 10 mounts a condenser microphone 11 composed of a stationary electrode 12 and a measuring diaphragm 13 fabricated from a suitable organic material (in the drawing said elements are shown with solid and dashed lines for simplicity). The conduit 8 is closed with a cover 14 sealed at the butt end of the conduit 8 by the use of a sealing ring 15.

In the preferred embodiment of the invention the conduit 8 has the length l exceeding 8 times its cross-sectional diameter d, while the volume $V_1$ of the conduit 8 is 50 times smaller than the volume V of the working chamber 1.

However, the length of the conduit may exceed 8 to 10 times its cross-sectional diameter, while the volume thereof may be at least 50 times smaller than the volume of the working chamber. The length and volume of the conduit are chosen to keep the temperature of the microphone 11 close to room temperature (normally about 293° C.) and to exclude the effect of molecular thermodiffusion on measuring accuracy.

The condition $l/d \geq 8-10$ is needed to increase the area of contact between the sample gas and the surface of the walls of the conduit 8 whereby heat transfer from the gas to the walls of the conduit 8 is appreciably improved. Also, the means for controlling temperature of the sample gas in the conduit 8 may be suitably located as will be described in more detail below. It should be noted that the above condition is preferably obtained by increasing the length of the conduit 8 instead of decreasing its cross-sectional diameter since in the latter case the sensitivity of the spectrophone may be substantially degraded due to attenuation of the acoustic signal passed through the narrow conduit 8.

At $l/d \leq 8$ the foregoing object is difficult to attain inasmuch as the operating temperature range of the spectrophone is decreased.

With the length of the conduit 8 satisfying the condition $l/d > 10$ the temperature range of the spectrophone may be increased. In this case, however, the sensitivity of the spectrophone is decreased substantially in proportion to the ratio $V/V_1$ due to increased ballast volume of the sample gas in the conduit 8, which is not subjected to laser radiation. Also, measuring accuracy is decreased under the effect of molecular thermodiffusion. This effect essentially consists in that molecules having different molecular weights are redistributed within the chamber 1 and the conduit 8 of the spectrophone due to the temperature gradient occurring in the gas, which is caused by the presence of zones in the vicinity of the microphone 11 and the windows 2, 3, wherein the temperature is close to room temperature. To decrease said effect upon measuring accuracy to quite a few percent, it is necessary to ensure that $V/V_1 \geq 50$, a condition which can be obtained by increasing the length of the working chamber 1. At $V/V_1 < 50$ measuring accuracy is decreased substantially in proportion to the ratio $V/V_1$. The above effect may be neglected at $V/V_1 > 50$. Certain limitations may, however, result due to excessive length of the spectrophone.

The microphone 11 is connected to a recording unit 17 through an electrical lead 16 in the cover 14. The working chamber 1 is filled with the sample gas as shown with the arrow B through a valve 18 mounted in a connection 19 communicating with the wider portion 9 of the conduit 8 through the cover 14.

The laser-excited spectrophone forming the subject of the present invention includes main means 20 and additional means 21 for controlling temperature of the sample gas in the working chamber 1 by its heating and cooling, respectively.

The main means 20 comprises a temperature control element in the form of a heater spiral 22 encompassing the outer walls of the chamber 1 and electrically coupled to the output of an individual thermoregulator 23 whose input is connected through a switch 24 to a temperature transducer 25 of the chamber 1, which is in direct contact with the wall of the chamber 1.

The additional means 21 comprises an individual temperature control element representing a chamber 26 encompassing the outer walls of the working chamber 1, a suitable coolant, say, liquid nitrogen vapours being passed between the inner walls thereof and the outer walls of the working chamber 1, and an individual thermoregulator 27 whose electrical input is coupled through the switch 24 to the temperature transducer 25 of the chamber 1, which is common to the additional means and the main means 20. The coolant outlet of the thermoregulator 27 is connected with the cavity of the chamber 26 through a connection 28, while its coolant inlet is coupled thereto through a connection 29, a feature assuring circulation of the coolant along a closed path.

Other electrical inputs of the thermoregulators 23 and 27 are connected to a programmed control unit 30 electrically coupled to the switch 24 and the recording unit 17.

The thermoregulators 23, 27, and the programmed control unit 30 are, respectively, such widely known units as a voltage regulator, a thermostat ensuring continuous pumping of coolant along a closed path, and a control unit normally included into the standard equipment of a laser-excited spectrophone.

The walls of the chamber 26 are protected against environmental effects by a thermal shield 31 surrounded by a common enclosure 32.

The ends of the heater spiral 22 and the leads of the temperature transducer 25 of the chamber 1 are passed through the walls of the chamber 26 and the shield 31 by the use of electrical leads 33 and 34, respectively.

The conduit 8 of the hereinproposed spectrophone includes two thermal filters 35 and 36 decreasing static temperature fluctuations of the sample gas in the vicinity of the microphone 11.

One, two or more thermal filters may be used to ensure a desired operating temperature range.

In the preferred embodiment of the invention the thermal filters 35 and 36 are perforated metal plates.

The filters may also represent fused metal balls, which is more effective as compared with the perforated metal plates in that heat dissipation is improved due to increased area of contact between the sample gas and the surface of the balls.

The laser-excited spectrophone in compliance with the present invention also includes a means 37 for controlling temperature of the sample gas in the conduit 8, which, respectively, cools or heats the sample gas in the conduit 8 depending on the operation of the main means 20 or the additional means 21 for controlling temperature of the sample gas in the working chamber 1, which heats or cools the sample gas in the working chamber 1.

The means 37 incorporates two temperature control elements encompassing the outer walls of the conduit 8. Said element represents a chamber 38 filled with a suitable coolant, say, water or liquid nitrogen vapours if the sample gas is cooled in the conduit 8 by the means 37 or a heater spiral 39 if the sample gas is heated in said conduit by said means. The means 37 also includes a temperature transducer 40 of the microphone 11 secured directly on said microphone 11 and thermoregulators 41 and 42 whose number corresponds to the number of the temperature control elements, the electrical inputs of said thermoregulators being connected to the temperature transducer 40 of the microphone 11 through a switch 43 electrically coupled to the programmed control unit 30. The coolant outlet of the thermoregulator 41 is connected with the cavity of the chamber 38 through a connection 44, while the coolant inlet thereof is connected with the same cavity of the chamber 38 through a connection 45. The output of the thermoregulator 42 is connected to the heater spiral 39.

The ends of the spiral 39 and the leads of the temperature transducer 40 of the microphone 11 are passed through the walls of the conduit 8 and its wider portion 9 by the use of electrical leads 46 and 47, respectively.

The thermoregulators 41 and 42 are constructionally similar to the thermoregulators 28 and 23, respectively.

To preclude damage to the optical windows 2 and 3 due to thermal strain, their temperature and the temperature of the microphone 11 are kept close to room temperature. This is done by surrounding the flanges 4 and 5, respectively, with heater spirals 48, 49 and chambers 50, 51 filled with coolant, say, water or liquid nitrogen vapours supplied into the cavities of the chambers 50, 51 through connections 52, 53 and flowing therefrom through connections 54, 55. Depending on the connection of the main means 20 or the additional means 21 for controlling temperature of the sample gas, which heats or cools the sample gas in the working chamber 1, the chambers 50, 51 or the heater spirals 48, 49 will be used.

The laser-excited spectrophone in compliance with the invention operates as follows.

During measurements, CW modulated laser radiation is passed through the optical windows 2 and 3 of the working chamber 1. As the laser radiation is periodically absorbed by the sample gas, there occur periodical fluctuations of gas temperature and, in effect, periodic fluctuations of gas pressure due to acoustic isolation of the working chamber 1 of the spectrophone, said pressure fluctuations being recorded by the microphone 11 as its capacitance changes with the sagging of the measuring diaphragm 13.

An electrical signal transmitted from the microphone 11 is detected and passed to the recording unit 17. The amplitude of said signal conveys information on the absorptivity of the sample gas and, hence, on the concentration of the molecules being detected in problems involving analysis of microimpurities in gases.

In accordance with the preset task the programmed control unit 30 sets conditions for changing temperature of the sample gas in the working chamber 1 of the spectrophone by applying control signals to the thermoregulators 23 or 27 depending on whether the sample gas is to be heated or cooled in the chamber 1 and to the switches 24, 43 connecting the temperatures transducers 25, 40, respectively, to the thermoregulators 23, 41 (position of the switches 24, 43 shown in the drawing) or to the thermoregulators 27, 42 (position of the switches 24, 43 not shown in the drawing).

Under the action of the control pulses the thermoregulator 23 or 27 changes the temperature of the walls of the chamber 1 by varying the voltage at the heater spiral 22 or the coolant flow in the chamber 26. Accordingly, the temperature of the sample gas in the working chamber 1 changes with the temperature of the walls of the working chamber 1. This permits measuring the amplitude of the acoustic signal with different discrete values of gas temperature or directly as a function of gas temperature as it changes continually.

Thermal diffusion in the gas with varying temperature causes heat transfer from the working chamber 1 to the microphone 11 whereby its temperature changes and, consequently, the varying parameters of the measuring diaphragm 13 adversely affect the normal operation of the microphone 11. Specifically, the sensitivity of the microphone may be changed. This effect is eliminated by force gas temperature control in the conduit 8. In the case of a comparatively narrow temperature range (on the order of ±50° K.) this is done by natural air cooling or heating of the gas in the conduit 8.

As the temperature range is increased further, say, to ±100° K. the thermal filters 35 and 36 will be activated with the result that the gas passing therethrough will be cooled or heated. Thus, relatively long conduit 8 and the thermal filters 35, 36 form a system effecting passive control of gas-temperature static distribution in the conduit 8. It should be noted that periodical acoustic oscillations occurring in the working chamber 1 during absorption of the laser radiation are transmitted essentially unattenuated to the microphone 11 through holes in the thermal filters 35, 36.

In operation over a wider temperature range the conduit 8 and the filters 35, 36 do not completely cool or heat the gas coming to the microphone 11 whereby the temperature of the microphone 11 will be changed. The temperature transducer 40 senses the indicated temperature variations and furnishes corresponding electrical signals to the thermoregulator 41 or 42 depending on whether the gas in the working chamber 1 is heated or cooled. In accordance with the level of said signals the thermoregulator 41 or 42 controls the means 37 for controlling temperature of the sample gas in the conduit 8, namely, the chamber 38 or the heater spiral 39 whereby the gas in the conduit 8 will be cooled or heated in a forced manner.

Thus, the temperature transducer 40, the thermoregulators 41, 42, and the temperature control elements, namely, the chamber 38 and the heater spiral 39 in the conduit 8 form a feedback system stabilizing the temperature of the microphone 11 at a fixed level close to room temperature. This permits maintaining the sensitivity of the microphone 11 essentially at the same level as the temperature of the gas in the working chamber 1 changes within wide limits. Physically, the operation of the spectrophone is based on transmission of periodical acoustic oscillations from the working chamber 1 to the microphone 11 through the gaseous medium in the conduit 8 possessing a noticeable static temperature gradient.

The laser-excited spectrophone forming the subject of the present invention allows analyzing absorption in a gaseous medium over a wide temperature range with the gas cooled to 100° K. or heated to 800° K. during an essentially unlimited time interval with high threshold sensitivity. For example, with a laser radiation power (energy) of 1 W (1 J) in the specified temperature range the hereinproposed spectrophone permits measuring absorptivities of $10^{-8}$ to $10^{-9}$ cm$^{-1}$, which corresponds to the detection limit of $10^{-7}$ to $10^{-8}$% in the case of many molecules.

Certain terms have been chosen to describe a preferred embodiment of the invention for clarity. The invention is not, however, limited to the exact terms used inasmuch as each term is understood to denote all equivalent elements functioning in a similar way and utilized for solving similar problems.

While it has been shown and described what is considered at present to be a preferred embodiment of the invention, modifications thereto will readily occur to those skilled in the art. It is not, therefore, desired that the invention be limited to the specific arrangement shown and described and it is intended to cover in the appended claims all such modifications that fall within the true spirit and scope of the invention.

What is claimed is:

1. A laser-excited spectrophone comprising:
   a working chamber whose cavity is formed with walls having inner and outer sides and also with first and second butt ends, said cavity being filled with a sample gas;
   a first optical window in the first butt end of said chamber, laser radiation being transmitted to said chamber through said window;
   a second optical window in the second butt end of said chamber, said window being used to remove said laser radiation from said chamber;
   a conduit formed with walls having outer and inner sides, which is in communication with the cavity of said working chamber and has a length exceeding 8 to 10 times its cross-sectional diameter, while a volume thereof is at least 50 times smaller than the volume of said working chamber;
   a condenser microphone mounted in said conduit; and
   a first means for controlling temperature of said sample gas in said working chamber by its heating, said means incorporating an individual temperature control element encompassing said outer side of said walls of said chamber, a temperature transducer of said chamber arranged on said outer side of said wall of said chamber, and an individual thermoregulator having a first input and an output and connected via its input to said temperature transducer of said chamber and via its output to the temperature control element thereof.

2. A laser-excited spectrophone as claimed in claim 1, which includes a second means for controlling temperature of said sample gas in said working chamber by its cooling, said second means incorporating an individual temperature control element encompassing said outer side of said walls of said chamber, and an individual thermoregulator having a first input and an output and connected via its input to said temperature transducer of said chamber, which is, thus, common to the first and second means, and via its output to the temperature control element thereof;
   an individual thermoregulator of the first means having a second input;
   an individual thermoregulator of the second means having a second input;
   a programmed control unit having first, second and third outputs and connected via its first output to the second input of said thermoregulator of the first means and via its second output to the second input of said thermoregulator of the second means; and
   a switch electrically coupled to the third output of said programmed control unit and connecting said temperature transducer of said chamber to said thermoregulator of the first means or to said thermoregulator of the second means in accordance with the command furnished by the programmed control unit.

3. A laser-excited spectrophone as claimed in claim 2, wherein said conduit includes at least one thermal filter decreasing static temperature fluctuations of said sample gas in the vicinity of said microphone.

4. A laser-excited spectrophone as claimed in claim 3, wherein said thermal filter represents a perforated metal plate.

5. A laser-excited spectrophone as claimed in claim 2, which includes another means for controlling temperature of said sample gas directly in said conduit by, respectively, cooling or heating said sample gas in said conduit depending on connection of the first or second means for controlling temperature of said sample gas in said working chamber.

6. A laser-excited spectrophone as claimed in claim 5, wherein said means for controlling temperature of said sample gas in said conduit comprises:
- a first temperature control element encompassing said outer side of said walls of said conduit;
- a second temperature control element encompassing said outer side of said walls of said conduit;
- a temperature transducer of said microphone mounted on said microphone;
- a thermoregulator of the first temperature control element having an input and an output and connected via its input to said temperature transducer of said microphone and via its output to the temperature control element thereof;
- a thermoregulator of the second temperature control element having an input and an output and connected via its input to said temperature transducer and via its output to the temperature control element thereof;
- said programmed control unit having a fourth output; and
- a switch electrically coupled to the fourth output of said programmed control unit and connecting said temperature transducer of said microphone to said thermoregulator of the first temperature control element or to said thermoregulator of the second temperature control element in accordance with the command furnished by said programmed control unit.

7. A laser-excited spectrophone as claimed in claim 1, wherein said conduit comprises at least one thermal filter decreasing static temperature fluctuations of said sample gas in the vicinity of said microphone.

8. A laser-excited spectrophone as claimed in claim 7, wherein said thermal filter represents a perforated metal plate.

9. A laser-excited spectrophone as claimed in claim 8, which includes another means for controlling temperature of said sample gas directly in said conduit by, respectively, cooling or heating said sample gas in said conduit depending on connection of the first or second means for controlling temperature of said sample gas in said working chamber.

10. A laser-excited spectrophone as claimed in claim 9, wherein said means for controlling temperature of said sample gas in said conduit comprises:
- a first temperature control element encompassing said outer side of said walls of said conduit;
- a second temperature control element encompassing said outer side of said walls of said conduit;
- a temperature transducer of said microphone mounted on said microphone;
- a thermoregulator of the first temperature control element having an input and an output and connected via its input to said temperature transducer of said microphone and via its output to the temperature control element thereof;
- a thermoregulator of the second temperature control element having an input and an output and connected via its input to said temperature transducer and via its output to the temperature control element thereof;
- said programmed control unit having a fourth output; and
- a switch electrically coupled to the fourth output of said programmed control unit and connecting said temperature transducer of said microphone to said thermoregulator of the first temperature control element or to said thermoregulator of the second temperature control element in accordance with the command furnished by said programmed control unit.

11. A laser-excited spectrophone as claimed in claim 7, which incorporates another means for controlling temperature, of said sample gas directly in said conduit by, respectively, cooling or heating said sample-gas in said conduit depending on connection of the first or second means for controlling temperature of said sample gas in said working chamber.

12. A laser-excited spectrophone as claimed in claim 11, wherein said means for controlling temperature of said sample gas in said conduit comprises:
- a first temperature control element encompassing said outer side of said walls of said conduit;
- a second temperature control element encompassing said outer side of said walls of said conduit;
- a temperature transducer of said microphone mounted on said microphone;
- a thermoregulator of the first temperature control element having an input and an output and connected via its input to said temperature transducer of said microphone and via its output to the temperature control element thereof;
- a thermoregulator of the second temperature control element having an input and an output and connected via its input to said temperature transducer and via its output to the temperature control element thereof;
- said programmed control unit having a fourth output; and
- a switch electrically coupled to the fourth output of said programmed control unit and connecting said temperature transducer of said microphone or to said thermoregulator of the first temperature control element or to said thermoregulator of the second temperature control element in accordance with the command furnished by said programmed control unit.

13. A laser-excited spectrophone as claimed in claim 1, which includes another means for controlling temperature of said sample gas directly in said conduit by, respectively, cooling or heating said sample gas in said conduit depending on connection of the first or second means for controlling temperature of said sample gas in said working chamber.

14. A laser-excited spectrophone as claimed in claim 13, wherein said means for controlling temperature of said sample gas in said conduit comprises:
- a first temperature control element encompassing said outer side of said walls of said conduit;
- a second temperature control element encompassing said outer side of said walls of said conduit;
- a temperature transducer of said microphone mounted on said microphone;
- a thermoregulator of the first temperature control element having an input and an output and connected via its input to said temperature transducer of said microphone and via its output to the temperature control element thereof;
- a thermoregulator of the second temperature control element having an input and an output and connected via its input to said temperature transducer and via its output to the temperature control element thereof;
- said programmed control unit having a fourth output; and a switch electrically coupled to the fourth output of said programmed control unit and connecting said temperature transducer of said microphone to said thermoregulator of the first temperature control element or to said thermoregulator of the second temperature control element in accordance with the command furnished by the programmed control unit.

* * * * *